US005683692A

United States Patent [19]

Taraschi et al.

[11] Patent Number: 5,683,692
[45] Date of Patent: Nov. 4, 1997

[54] USE OF RIPONUCLEASES FOR TREATING PARASITIC AND VIRAL DISEASES

[75] Inventors: Theodore Taraschi, Medford, N.J.; Emmanuelle Nicolas, Philadelphia, Pa.

[73] Assignee: Thomas Jefferson University, Philadelphia, Pa.

[21] Appl. No.: 473,770

[22] Filed: Jun. 6, 1995

[51] Int. Cl.$^6$ .................... A61K 38/46; A61K 38/16; A61K 38/00; A61K 39/395
[52] U.S. Cl. .................... 424/94.6; 514/8; 514/12; 514/895; 424/183.1; 530/370
[58] Field of Search ................ 514/8, 12, 895; 530/370; 424/195.1, 94.6, 183.1; 435/258.2

[56] References Cited

U.S. PATENT DOCUMENTS 4,795,739  1/1989  Lifson et al. ...................... 514/8

OTHER PUBLICATIONS

Cenini et al. Effect of ribosome–inactivating proteins on ribosomes from *Tetrahymena pyriformis* and *Acathamoeba castellanii*, Biochem. Biophys. Res. Commu. 148(2):521–526 Oct. 29, 1987.
Barbieri et al., "Ribosome–inactivating proteins from plants", *Biochim. Biophys. Acta* 1993, 1154, 237–282.
Brinkmann, U. and Pastan, I., "Immunotoxins against cancer", *Biochim. Biophys. Acta* 1994, 1198, 27–45.
Huang et al., "Anti–HIV plant proteins catalyze topological changes of DNA into inactive forms", *BioFactors.* 1992, 4, 37–41.
Gormley et al., "Trafficking of Malarial Proteins to the Host Cell Cytoplasm and Erythrocyte Surface Membrane Involves Multiple Pathways", *J. Cell. Biol.* 1992, 119, 1481–1495.
Lee–Huang et al., "Human immunodeficiency virus type 1 (HIV–1) inhibition, DNA–binding, RNA–binding, and ribosome inactivation activities in the N–terminal segments of the plant anti–HIV protein GAP31", *Proc. Natl. Acad. Sci. USA* 1994, 91, 12208–12212.
Lee–Huang et al., "MAP 30: a new inhibitor of HIV–1 infection and replication", *FEBS Let* 1990, 272, 12–18.
Lee–Huang et al., "A new class of anti–HIV agents: GAP31, DAPs 30 and 32", *FEBS Let* 1991, 291, 139–144.
Ling et al., "Cleavage of supercoiled double–stranded DNA by several ribosome–inactivating proteins in vitro", *FEBS Let* 1994, 345, 143–146.
Li et al., "Trichosanthin, a potent HIV–1 inhibitor, can cleave supercoiled DNA in vitro", *Nucleic Acids Res.* 1991, 19, 6309–6312.
Rybak et al., "In vitro anti–tumor activity of the plant ribosome inactivating proteins MAP30 and GAP31", *Int. J. Oncol.* 1994, 5, 1171–1176.
Stirpe et al., "Gelonin, a New Inhibitor of Protein Synthesis, Nontoxic to Intact Cells", *J. Biol. Chem.* 1980, 255, 6947–6953.

*Primary Examiner*—Robert A. Wax
*Assistant Examiner*—Tekchand Saidha
*Attorney, Agent, or Firm*—Law Offices of Jane Massey Licata

[57] ABSTRACT

A method of treating viral and protozoal infections using RIPonucleases is provided.

2 Claims, 4 Drawing Sheets

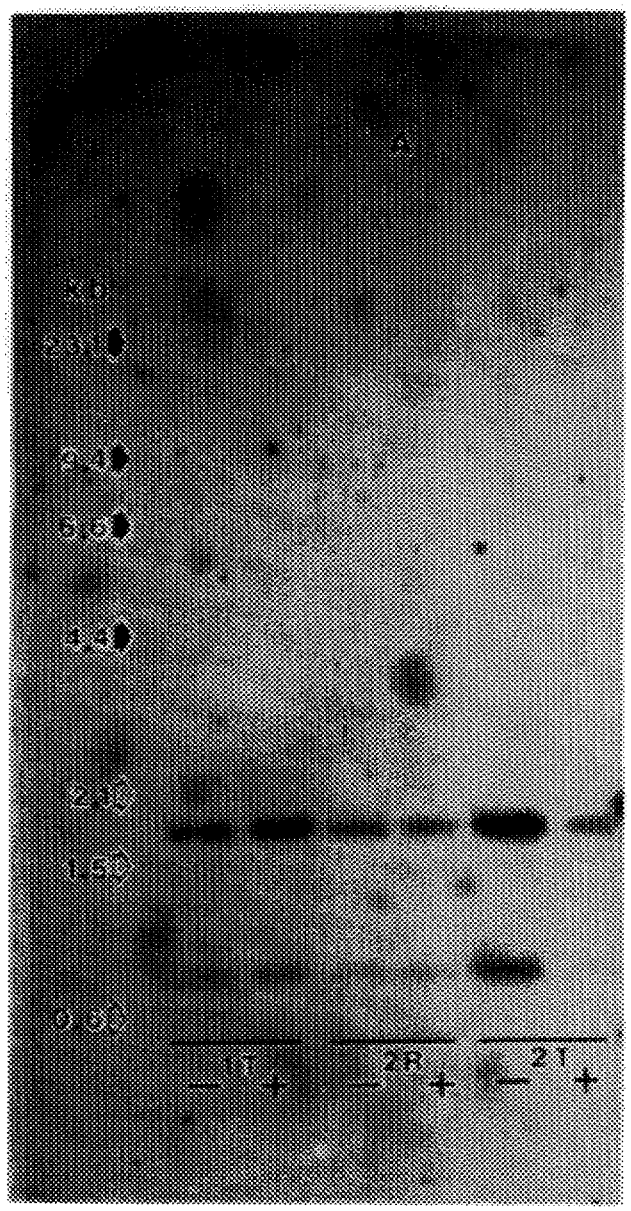 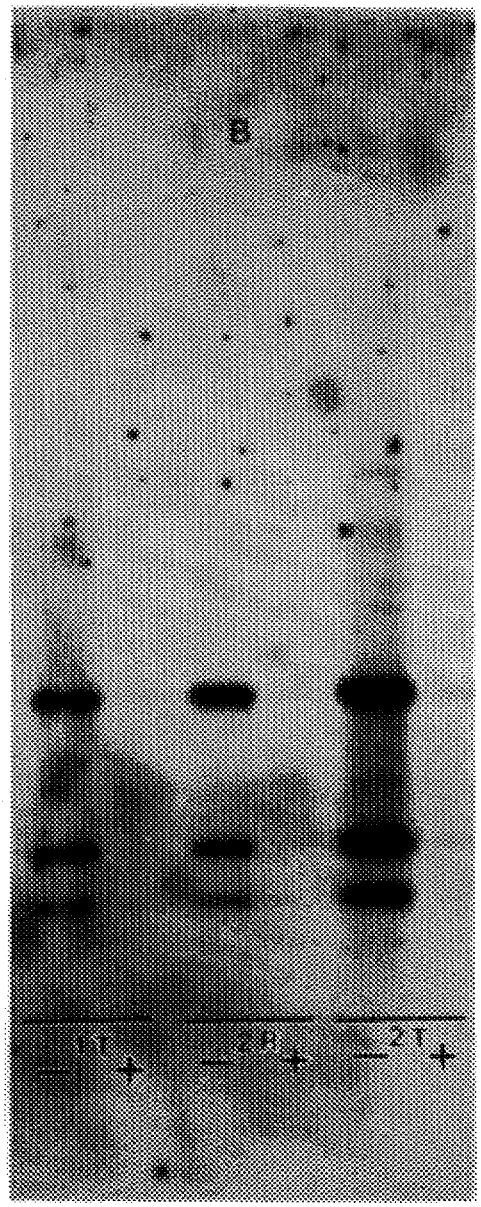
FIG. 3A       FIG. 3B

USE OF RIPONUCLEASES FOR TREATING PARASITIC AND VIRAL DISEASES

BACKGROUND OF THE INVENTION

A pressing need exists to develop new antiparasitic and antiviral agents. The limited array of efficacious chemotherapeutic agents will shortly outlive their usefulness due to the development of drug resistance. For example, *Plasmodium falciparum*, the most dangerous of the human malaria parasites, has developed resistance to all the widely available anti-malarial agents.

Ribosome-inactivating proteins (RIPs) from plants have an RNA N-glycosidase activity that depurinates the major rRNA, thus, damaging ribosomes and arresting protein synthesis. Class I RIPs (e.g., gelonin, saporin, momordin and trichosanthin) are single chain, basic proteins having molecular weights of about 30 kDa. They are potent inhibitors of protein synthesis in cell-free systems, but are relatively non-toxic to intact cells or animals. They are of current interest in different areas including anti-HIV therapy (Lee-Huang et al. *Proc. Natl. Acad. Sci. USA* 1994, 91, 12208–12212; Lee-Huang et al., *FEBS Let* 1990, 272, 12–18; Lee-Huang et al., *FEBS Let* 1991, 291, 139–144) and the construction of "magic bullets" with anti-tumor activity (Barbieri et al., *Biochim. Biophys. Acta* 1993, 1154, 237–282; Brinkmann, U. and Pastan, I., *Biochim. Biophys. Acta* 1994, 1198, 27–45).

Ribosome inactivation has been commonly accepted as the mechanism through which RIPs exert their cytotoxic effects. However, in instances where antiviral activity has been observed, the origin of the RIP cytotoxicity cannot be attributed to inhibition of protein synthesis. In recent years, RIPs have been described to possess an additional enzymatic activity which cleaves circular DNA to produce nicked circular and linear DNA. This endonuclease activity has been described for ricin A chain (Ling et al., *FEBS Let* 1994, 345, 143–146), trichosanthin (Li et al., *Nucleic Acids Res.* 1991, 19, 6309–6312), and GAP 31 (Huang et al., *BioFactors*. 1992, 4, 37–41). Trichosanthin has shown some promise in phase II trials on AIDS patients. GAP 31 has been reported to have anti-HIV activity in vitro. Some investigators suggest that GAP 31 may be cytotoxic by acting as a topoisomerase poison (Rybak et al., *Int. J. Oncol.* 1994, 5, 1171–1176; Lee-Huang et al., *Proc. Natl. Acad. Sci. USA* 1994, 91, 12208–12212) because topoisomerases play important roles in DNA replication and repair. To date, it has not been demonstrated that GAP 31 acts as a topoisomerase poison in cells either in vitro or in vivo.

It has now been found that the interaction of class I RIPs, including gelonin, recombinant gelonin, momordin, saporin and trichosanthin, and the A chain of class II RIPs, including ricin and recombinant ricin, is not restricted to circular, double-stranded DNA as previously reported. It has also been found that class I RIPs and the A chain of class II RIPs also exert endo- and exo-nuclease activity on linear DNA. Since class I RIPs and the A chain of class II RIPs have been found to possess multiple enzymatic properties (e.g., ribosome inactivation and nuclease activities), these toxins are identified as "RIPonucleases" in the present invention.

SUMMARY OF INVENTION

The present invention concerns the use of RIPonucleases for treating pathologic organisms containing extracellular DNA or RNA. These organisms include, but are not limited to, DNA viruses such as herpes simplex, Epstein-Barr, hepatitis B and papilloma virus; retroviruses, including HIV; protozoans such as Plasmodium and Leishmania; and certain cancers, including, but not limited to, osteogenic sarcoma and small cell lung cancers that also have episomal extrachromosomal DNA.

DESCRIPTION OF THE DRAWINGS

FIG. 3 shows the results of a Southern blot analysis of 35 and 6 kb DNA from IRBC treated with gelonin. IRBC were untreated (−) or treated (+) with gelonin ($1\times10^{-6}$ M) beginning at the ring stage (i.e., 8–10 h post-invasion) for 24 hours. IRBC were withdrawn from culture at the end of the first erythrocytic cycle (1T) and at 10 (2R) and 30 h (2T) post-invasion in the second cycle and embedded in low melting agarose. Following treatment with proteinase K, the blocks were digested with Hind III. DNA digests were electrophoretically separated using a 0.8% Seakem Gold agarose gel, transferred onto Zeta Probe and hybridized with either a 700 bp segment that spans part of the small subunit rRNA gene of the 35 kb Plasmodial DNA (A) or with the complete mitochondrial genome (B), radiolabeled with 32P by random priming. T stand for trophozoite stage while R stands for ring stage.

DETAILED DESCRIPTION OF THE INVENTION

The invention provides a method for treating human malarias with RIPonucleases including, but not limited to, a class I RIP or the A chain of a class II RIP. Examples of such RIPs include, but are not limited to, gelonin, saporin, momordin, trichosanthin, recombinant gelonins (rGel) or variants of recombinant gelonin, including rGelN239C and rGelN247C, or ricin or recombinant ricin. Unconjugated RIPonucleases or RIPonucleases conjugated to selected antibodies or ligands may be used in the present invention.

Intravenous or intraperitoneal administration, either as a bolus injection or by continuous infusion, is preferred.

A method of treating viral and protozoal infections with RIPonucleases is also provided. In this method an animal infected with a viral or protozoal infection is administered an effective amount of a selected RIPonuclease. Unconjugated RIPonucleases or RIPonucleases conjugated to selected antibodies or ligands may be used. By "effective amount" it is meant a concentration of a selected RIPonuclease capable of killing cells infected with a virus or protozoa. Effective amounts can be routinely determined by those of skill in the art. Intravenous or intraperitoneal administration is preferred in this embodiment of the invention. By "animal" it is meant to include, but is not limited to, mammals, most preferably, humans.

A method of treating organisms and cells containing extrachromosomal DNA or RNA is also provided. These include, but are not limited to, DNA viruses such as herpes simplex, Epstein-Barr, hepatitis B and papilloma virus; retroviruses such as HIV; protozoans such as Plasmodium and Leishmania; and certain cancers, including osteogenic sarcoma and small cell lung cancer.

The use of RIP-inactivated RIPonucleases in treating cells or organisms with extrachromosomal DNA or RNA is also provided in the present invention.

Treatment of *Plasmodium falciparum* with Gelonin

Figure 1:
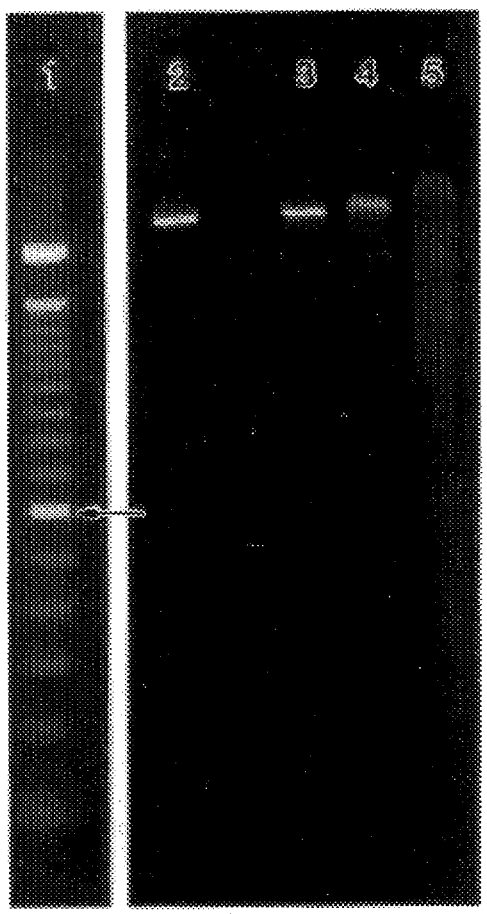
FIG. 1 shows the effect of gelonin on a 2.7 kb linear DNA. Linear DNA was incubated at 32° C. for 1 hour with gelonin in 50 mM NaCl, 10 mM Tris-HCl, and 5 mM $MgCl_2$, pH 7.9. DNA was analyzed on a 1.5% Trevigel gel. Lane 1, 100 bp ladder; the position of 600 bp DNA is indicated with an arrow; Lane 2, 0.2 µg of 2.7 kb linear DNA. Lanes 3, 4 and 5, plant gelonin at 0.4, 1 and 2 µg per 0.2 µg DNA, respectively. Gels are stained with ethidium bromide.
Figure 2A:
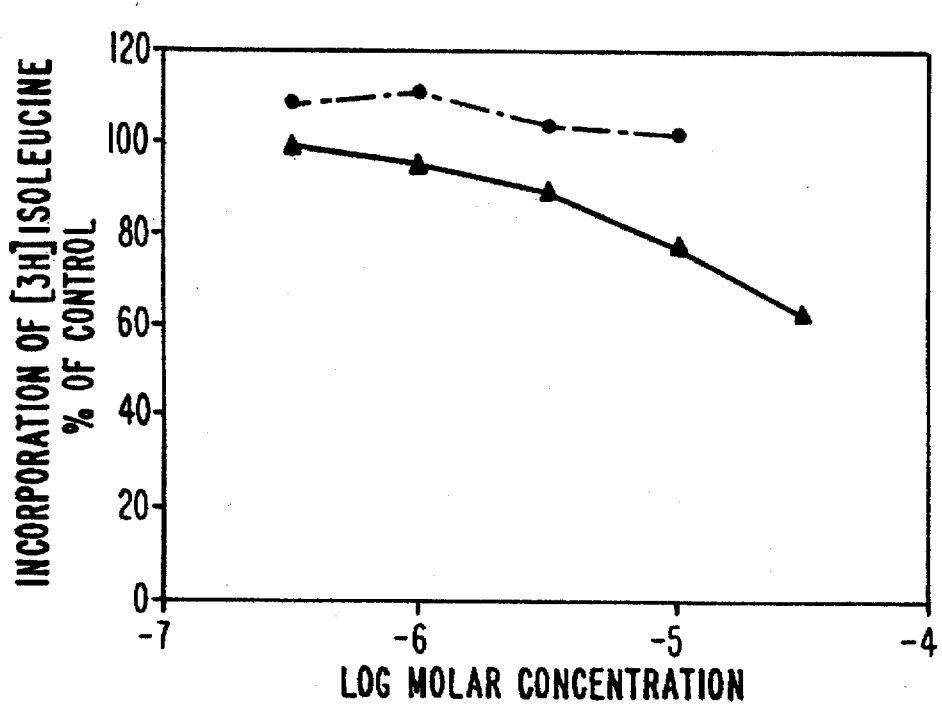
FIG. 2 shows inhibition of parasite protein and nucleic acid synthesis by gelonin and heat-inactivated gelonin. [$^3$H]isoleucine (left) and [$^3$H]hypoxanthine (right) were used to measure protein and nucleic acid synthesis, respectively. In the top panel, cell cultures ($10^8$ cells, 3% hematocrit, 2% parasitemia) were exposed to various concentrations of gelonin (untreated depicted as solid line; heat-inactivated depicted as broken line) at 5+ or −3 hours post-invasion. At 29 hours post-invasion, 20 µl of [$^3$H] isoleucine or [$^3$H]hypoxanthine were added to each well. Following a 4 hour pulse, the cultures were transferred to 1 ml of 20% (protein) or 5% (nucleic acid) TCA. The solution was incubated for 10 minutes on ice and the cells pelleted by centrifugation. The pellet was washed twice with 10% or 5% TCA, dissolved in 0.2 M NaOH and added to 10 ml of Budget Solve scintillation fluid for radioactivity counting. Data are expressed as % incorporation of radioactive label into toxin-treated cells relative to control cells (no toxin). In the bottom panel, cells were exposed to gelonin as described above and washed at 35 hours post-invasion. The parasitemia was reduced five times by the addition of uninfected erythrocytes. The cells were returned to culture in toxin-free medium. They were labeled and harvested 45 hours later than in the top panel.
Figure 2B:
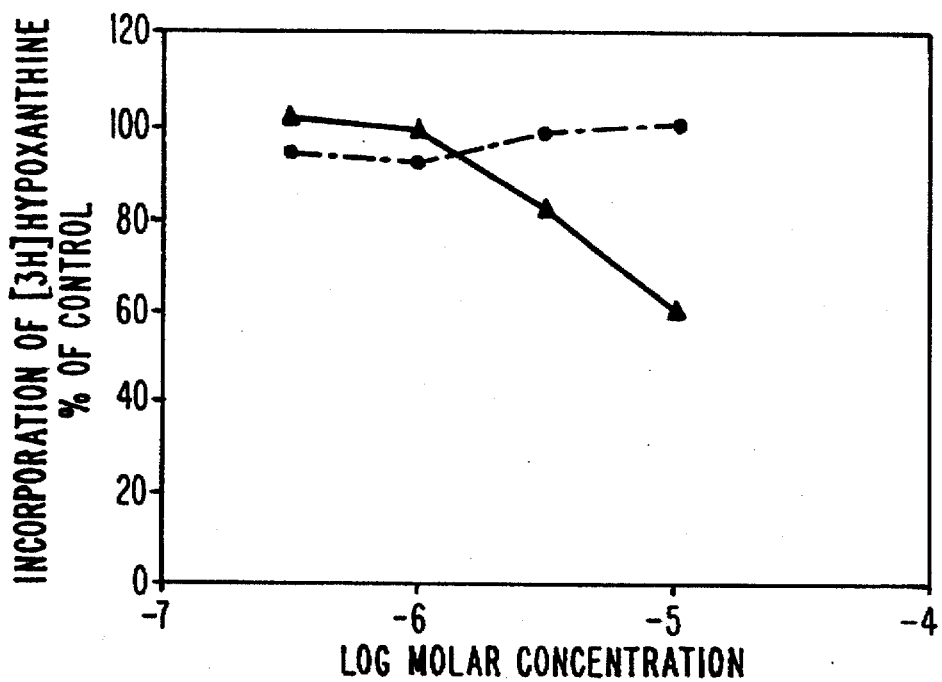
Figure 2C:
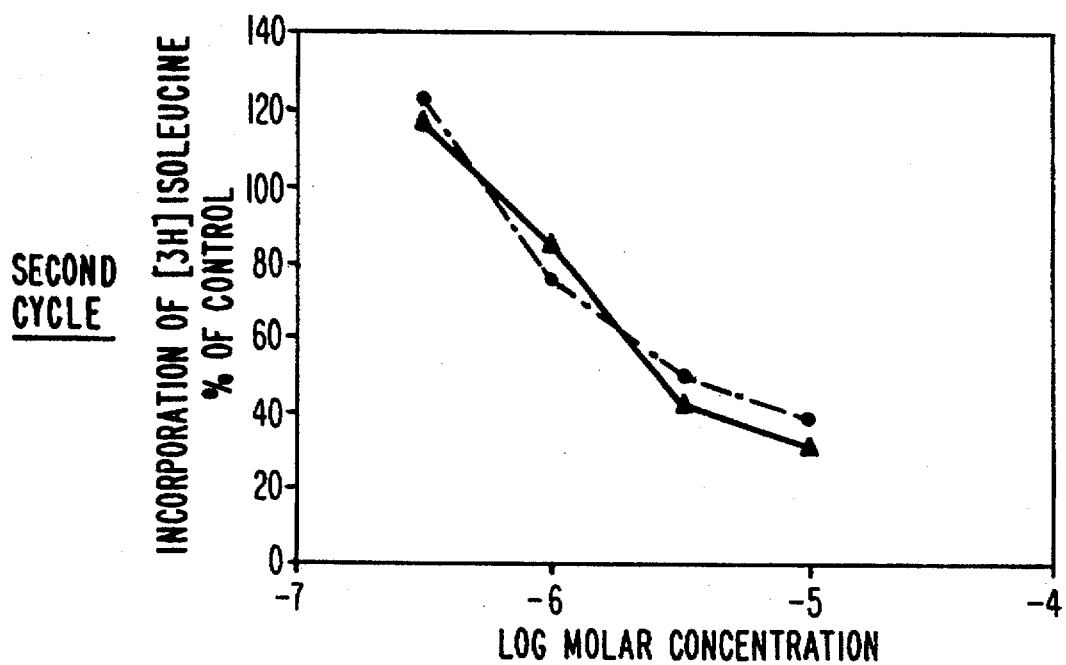
Figure 2D:
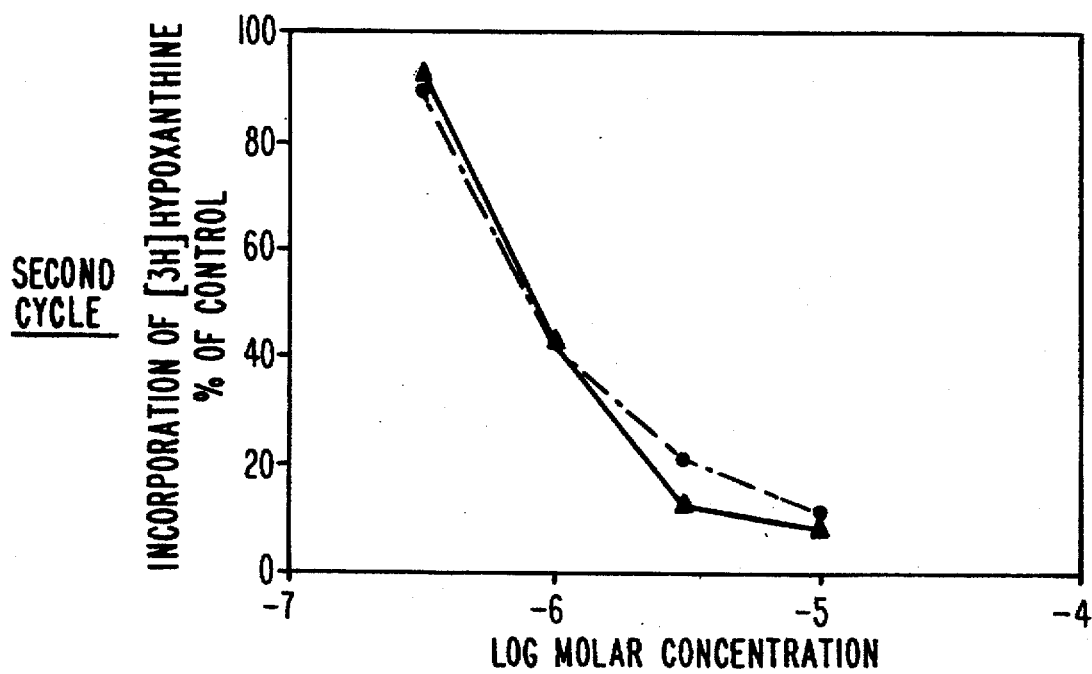

Evidence that RIPonucleases are cytotoxic by damaging extrachromosomal DNA was obtained from experiments wherein cultured intraerythrocytic malaria parasites were treated with gelonin. In addition to genomic DNA, malaria parasites contain two extrachromosomal DNAs; a 35 kb cytoplasmic, circular DNA and a 6 kb tandemly repeated mitochondrial DNA. It was observed that gelonin had a more pronounced effect on parasite nucleic acid synthesis than parasite protein synthesis. To separate these effects, a procedure was devised to remove the RIP activity while maintaining endo- and exo-nuclease activity. This involved heating gelonin at 80° C. for 15 minutes. RIP-inactivated gelonin was determined to be cytotoxic to intracellular malaria parasites (FIG. 2). Other methods of inactivating the RIPonuclease to remove the ribosome inactivating property include, but are not limited to, genetic mutation and chemical modification. Killing of parasites was found to be associated with degradation of parasite 6 kb mitochondrial DNA (FIG. 3).

It is believed that the anti-vital activity of RIPs is due to nuclease effects on vital DNA before it integrates into the host genome. While nuclear DNA is likely to be protected from nuclease activity due to its remote location in the cell and the protective shell provided by histones, it is believed that vital DNA (or possibly RNA) in the host cell cytosol is vulnerable to RIPonuclease binding and degradation. Since normal cells do not possess extrachromosomal DNA in the cytosol, they would be unaffected by RIPonucleases. RIPs are not toxic to non-pathologic cells. Further, since multidrug resistance (mdr) p-glycoproteins responsible for drug resistance do not exclude macromolecules from cells, and RIPonucleases are macromolecules, development of drug resistance to these agents, which has plagued treatment of pathogenic organisms and malignancies, is not expected.

Identification of the Nuclease Activity of RIPonucleases

To determine if gelonin formed a covalent complex with DNA, similar to topoisomerases, gelonin was incubated with $^{12}P$-labeled linear DNA. Analysis by gel electrophoresis revealed the presence of a low-migrating band. Migration of gelonin at this level of the gel was confirmed by Western blot analysis. The formation of this complex was observed with linear DNA from three different sources. While the addition of 50 times excess of cold DNA prior to the addition of radioactive DNA prevented the observation of a DNA-gelonin complex, it had no effect when performed after 45 minutes of incubation. The complex was not observed when SDS was omitted or when the sample was chilled on ice before loading. These results indicate that the complex is not covalent. The complex formed between gelonin and DNA is different from the cleavable complexes described for topoisomerases. These results, and the fact that the DNA cleavage by RIPs is observed even in the absence of protein denaturant strongly suggest that gelonin or GAP 31 are not cytotoxic to cells due to a topoisomerase poison-like activity as has been suggested previously (Lee-Huang et al., *Proc. Natl. Acad. Sci. USA* 1994, 91, 12208–12212).

This gel also revealed the presence of a radioactive band in the front of the gel, providing evidence for exonuclease activity. To establish this activity, quantitative analysis of the solubilization of 5' or 3' end-labeled DNA was performed. It was determined that both plant RIPs (e.g., gelonin) and the recombinant gelonins rGel, rGel N239C and rGel N247C possess 5'-3' and 3'-5' exonuclease activity on linear DNA. The kinetics of degradation indicated that the reaction was progressive, consistent with the observation of a complex by the gel-shift assay.

It has been reported (Ling et al., FEBS Let 1994, 345, 143–146) that the endonuclease activity of ricin-A chain on supercoiled DNA is largely retained, even if the protein is boiled, a treatment that is known to entirely inactivate its RNA N-glycosidase activity. In order to determine if RIP-inactivated gelonin had exonuclease activity, the nuclease assay was performed with rGel N239C and plant gelonin after heating at 80° C. for 15 minutes. While RIP activity was eliminated, endo- and exo-nuclease activities remained.

Therefore, class I plant RIPs and recombinant gelonins possess dual enzymatic activities, i.e., inhibition of protein synthesis and endo-and exo-nuclease activity on supercoiled, circular and linear DNA. The RIP activity can be eliminated with heat treatment, without sacrificing nuclease activity. This may be important for eliminating unwanted, non-specific cytotoxicity noted in humans administered trichosanthin.

Effects of Gelonin on Parasite Growth

To determine whether gelonin added to the external medium of cultured infected red blood cells (IRBC) could gain access to the parasite cytoplasm in a functional state, various concentrations of gelonin were added to infected erythrocytes during the ring stage. The effect on parasite protein and nucleic acid syntheses were determined by measuring the incorporation of [$^3$H]isoleucine at the trophozoite stage when the synthesis in untreated parasites is known to be maximal. As shown in FIG. 2 (Top panel), gelonin was found to strongly inhibit parasite protein synthesis in a concentration dependent fashion. A gelonin-free sample prepared by filtration through a 10,000 M. W. cut-off filter was found to be inactive, demonstrating that toxicity is not due to a low molecular weight contaminant.

Effects of Gelonin on Parasite Morphology

The morphology of IRBC taken from gelonin-treated or untreated cultures at 29 hours post-invasion was analyzed by transmission electron microscopy. Untreated cells displayed morphology typical of healthy, trophozoite stage infections. A large nucleus, food vacuole containing degraded hemoglobin (hemozoin) and a double membrane vesicle containing ingested hemoglobin were visible. By contrast, parasites in IRBC that were incubated with a toxic dose ($2\times10^{-5}$ M) of gelonin were very small and poorly organized, indicative of cell death.

Immunolocalization of Gelonin in IRBC IRBC incubated under the experimental conditions described were also examined by immunoelectron microscopy. Sections of gelonin-treated IRBC were incubated with an anti-gelonin antibody and an appropriate gold-labeled secondary antibody. Gold particles were localized exclusively to the parasite compartment. No gold particles were observed in the host cell cytosol or associated with uninfected cells. No reactivity was observed with control IRBC, indicating that there is no non-specific reactivity with infected cells.

Long Term Effects of Gelonin Treatment on Parasite Growth

Ring stage IRBC were incubated with increasing concentrations of gelonin or RIP-inactivated gelonin, washed and suspended in toxin-free medium at the schizont stage. Protein and nucleic acid syntheses were measured at 29 hours post-invasion in the second erythrocytic cycle. The results shown in FIG. 2 (Bottom panel) suggest that gelonin internalized by parasites during the first cycle caused further cytotoxicity. In order to characterize the second cycle effect, the effect of an exposure to $1\times10^{-6}$ M gelonin was further studied. This concentration was chosen because whereas it had little effect on protein or nucleic acid synthesis during the first cycle, the incorporation of [$^3$H]hypoxanthine measured in the second cycle was only 40% of the control value. Examination of Giemsa-stained blood smears from the control and gelonin-treated cultures at the ring stage in the second cycle revealed that the low incorporation of [$^3$H] hypoxanthine was not due to reduced parasite invasiveness, as the parasitemia of control and treated cultures was similar. Gelonin treatment did not appear to effect the synchrony of the infection. Electron microscopic examination of the new ring-stage infections revealed no striking morphological abnormalities in the treated parasites. At the trophozoite stage, untreated IRBC had a morphology characteristic of healthy, mature trophozoites, whereas the gelonin-treated IRBC were small and poorly developed, indicative of cell injury. The presence of a food vacuole in the treated parasites suggested that while gelonin was cytotoxic, it did not arrest all events associated with parasite development. This "second cycle" effect was also obtained by treatment with RIP-inactivated gelonin (FIG. 2, Bottom panel) suggesting that nuclease activity of gelonin is responsible for cytotoxicity.

Characterization of the effects of gelonin on malarial DNA

IRBC treated with gelonin ($1\times10^{-6}$ M) for 24–30 hours beginning at the ring stage were withdrawn from culture at the end of the first erythrocytic cycle or at 8 or 30 hours post-invasion in the second cycle and embedded in low melting agarose. Following treatment with proteinase K, the blocks were digested with Hind III. DNA digests were electrophoretically separated using a 0.8% Seakem Gold (FMC Corp. New York, N.Y.) agarose gel, transferred onto Zeta Probe (Bio Rad, Hercules, Calif.) and hybridized with either a 700 bp segment that spans part of the small subunit rRNA gene of the 35 kb plasmodial DNA or with the complete mitochondrial genome, radiolabeled with $^{32}$P by random priming. Treatment of 35 kb DNA with HindIII produces bands at 0.850 and 1.875 kb; treatment of 6 kb DNA with HindIII produces bands at 3.059, 1.644 and 1.263 kb. Whereas genomic DNA and the 35 kb DNA were unaltered by treatment of IRBC with gelonin, the 6 kb DNA was essentially eliminated (FIG. 3). This could be due either to nuclease digestion or prevention of mitochondrial replication. In any case, gelonin-treated parasites die in the second life cycle and parasitemia is eliminated. Thus, RIP-inactivated RIPonucleases have utility for treating malaria.

The invention is further described in the following non-limiting examples.

EXAMPLES

EXAMPLE 1

Materials

Gelonin (Lot 121H4035) was obtained from Sigma Chemical Co. (St. Louis, Mo.). L-[4,5-$^3$H]isoleucine ($10^2$ Ci/mmol) was obtained from Amersham (Arlington Heights, Ill.). Budget Solve was from Research Products International Corp. (Mount Prospect, Ill.). The gold-labeled (20 nm size particle), goat anti-rabbit (Fc specific) IgG antibody used for immunoelectron microscopy was obtained from E.Y. Laboratories (San Mateo, Calif.).

Gelonin was resuspended in phenol red-free culture medium and sterile filtered with a 0.22 μm cellulose acetate syringe tip filter (Costar, Cambridge, Mass.). Protein concentrations were determined by absorbance measurements using E of a 1% solution at 280 nm=6.7 as described by Stirpe et al. *J. Biol. Chem.* 1980, 255, 6947–6953.

EXAMPLE 2

Preparation of RIPonucleases without RIP Activity

The RIP activity of gelonin is removed by heating at 80° C. for 15 minutes. More than 50% of the nuclease activity remains after heat inactivation. While RIPs such as ricin A chain, gelonin and trichosanthin have been safely administered to humans, some cytotoxicity is encountered. It is believed this non-specific toxicity is due to the RIP activity of RIPonucleases, therefore, elimination of RIP (but not nuclease activity) leaves the RIPonucleases efficacious, while greatly reducing or eliminating non-specific toxicity.

EXAMPLE 3

Cell culture

Clone 5 of the FCR Gambian strain of *Plasmodium falciparum* was grown and the infections synchronized as described by Gormley et al. *J. Cell. Biol.* 1992, 119, 1481–1495, however, the stock culture was maintained in an atmosphere of 5% $CO_2$/5% $O_2$/90% $N_2$.

EXAMPLE 4

Determination of the Effect of Gelonin on Parasite Protein and DNA Synthesis During One Erythrocytic Cycle

[$^3$H]isoleucine and [$^3$H]hypoxanthine were used to measure protein and nucleic acid synthesis, respectively. These markers have been established as the benchmark for determining parasite growth. Experiments were conducted in 96-well plates that were maintained in candle jars. Each experimental condition was done in triplicate. Cells were cultured in hypoxanthine-free tissue culture medium. Cell cultures ($10^8$ cells, 3% hematocrit, 2% parasitemia) were exposed to various concentrations of gelonin ($5\times10^{-7}$–$2\times10^{-5}$ M) at 5 (+or −3) hours post-invasion. Untreated (control) cultures received toxin-free medium. At 29 hours post-invasion, 20 μl of [$^3$H]isoleucine (60 Ci/ml) or [$^3$H]hypoxanthine (30 Ci/ml) were added to each well. Following a 4 hour pulse, the [$^3$H]isoleucine-labeled cultures were diluted 1:1 with $H_2O$ and transferred to 1 ml of 20% trichloracetic acid (TCA). After an incubation for 10 minutes on ice, the cells were centrifuged. The pellet was washed twice with 10% TCA, dissolved in 0.2 M NaOH and added to 10 ml of Budget Solve scintillation fluid for radioactivity counting. The [$^3$H]hypoxanthine-labeled cultures were harvested as described for the [$^3$H]isoleucine-labeled cultures except that 5% TCA was used to wash the pellet. Data are given as percent incorporation of radioactive label into toxin-treated cells relative to control cells (no toxin).

EXAMPLE 5

Long Term Effects of Gelonin Treatment on Parasite Growth

To assess the effect of gelonin on parasite growth during the subsequent erythrocytic cycle, IRBC were exposed to gelonin as described in Example 4 and washed at 35 hours post-invasion. The parasitemia was reduced five times by the addition of uninfected erythrocytes. The cells were returned to culture in toxin-free medium. At 29 hours post-invasion of the second erythrocytic cycle (control IRBC were in the trophozoite stage), [$^3$H]hypoxanthine was added to all the wells. Radioisotopically labeled IRBC were harvested as described for the measurement at the first cycle.

EXAMPLE 6

Electron microscopy

For analysis of ultrastructural morphology, cells were fixed in 2% glutaraldehyde, 1% tannic acid, 4% sucrose in 0.05 M sodium phosphate buffer (PB), pH 7.4, for 1.5 hours at room temperature. They were post-fixed in 2% osmium tetroxide, 0.05 M PB, pH 7.4 for 1.5 hours at 4° C. After staining with 1% uranyl acetate, cells were pelleted in 2% agarose. The pellets were dehydrated in graded acetone and embedded in Spurts. Sections (60 nm thick) were cut on a Reicheft Ultracut E microtome. After staining in 2% uranyl acetate in 50% ethanol and Reynolds lead, sections were examined with a Hitachi 7000 scanning transmission electron microscope.

EXAMPLE 7

Immunoelectron Microscopy

Cells were fixed in 1% paraformaldehyde, 0.1% glutaraldehyde, and 0.1 M PB, pH 7.4, for 15 minutes at 4° C. They were washed in PB and pelleted in 2% agarose. Samples were dehydrated in 70% ethanol and embedded in London Resin (LR) White which was polymerized at 45° C. for 4 days. Sections (80 nm thick) were picked up on 200 mesh carbon coated nickel grids. Antibody incubations were performed at room temperature. Grids were floated on 0.1 M PB, 1% dried nonfat milk, and 0.01% Tween-20 (PB-milk-Tween) for 1.5 hours. They were floated overnight in a wet atmosphere chamber on an anti-gelonin antibody solution (0.02 mg/ml in PB-milk-Tween) or on PB-milk-Tween (as a control). After washing in PB-milk-Tween, grids were exposed to gold (20 nm)-labeled, goat anti-rabbit IgG antibody diluted 1:20 in PB-milk-Tween for 3 hours. Grids were washed, stained by successive incubations in 2% glutaraldehyde, 1% osmium tetroxide, and 2% uranyl acetate in 50% ethanol and Reynolds lead.

What is claimed:

1. A method of treating a viral or protozoal infection in an animal wherein extrachromosomal viral or protozoal DNA or RNA is present in infected cells of the animal comprising administering an mount of a selected RIPonuclease to the animal effective to damage the extrachromosomal DNA or RNA and kill the virus or protozoan causing the infection wherein the selected RIPonuclease is heat inactivated to remove the ribosome inactivating property of the RIPonuclease.

2. The method of claim 1 wherein the animal is infected with *Plasmodium falciparum* and the selected RIPonuclease is gelonin.

* * * * *

UNITED STATES PATENT AND TRADEMARK OFFICE
CERTIFICATE OF CORRECTION

PATENT NO. : 5,683,692

DATED : November 4, 1997

INVENTOR(S) : Taraschi et al.

It is certified that error appears in the above-indentified patent and that said Letters Patent is hereby corrected as shown below:

At col 3, line 64, please delete "$^{12}$P-labeled" and insert therefor --$^{32}$P-labeled--.

At col 7, line 31, please delete "Spurts." and insert therefor --Spurrs.--.

At claim 1, col. 8, line 25, please delete "mount" and insert therefor --amount--.

Signed and Sealed this

Thirty-first Day of March, 1998

Attest:

BRUCE LEHMAN

*Attesting Officer*  *Commissioner of Patents and Trademarks*